(12) United States Patent (10) Patent No.: US 9,037,245 B2
Sharma et al. (45) Date of Patent: May 19, 2015

(54) ENDOSCOPIC LEAD IMPLANTATION METHOD

(75) Inventors: Virender K. Sharma, Paradise Valley, AZ (US); Shai Policker, Tenafly, NJ (US); Paul V. Goode, Cherry Hill, NJ (US); Bevil Hogg, Soquel, CA (US)

(73) Assignee: EndoStim, Inc., St. Louis, MO (US)

( * ) Notice: Subject to any disclaimer, the term of this patent is extended or adjusted under 35 U.S.C. 154(b) by 0 days.

(21) Appl. No.: 13/602,184

(22) Filed: Sep. 2, 2012

(65) Prior Publication Data

US 2013/0090551 A1 Apr. 11, 2013

Related U.S. Application Data

(60) Provisional application No. 61/530,781, filed on Sep. 2, 2011.

(51) Int. Cl.
*A61B 1/00* (2006.01)
*A61B 1/273* (2006.01)
*A61B 5/06* (2006.01)
(Continued)

(52) U.S. Cl.
CPC ........... *A61B 1/00087* (2013.01); *A61B 1/2733* (2013.01); *A61B 5/06* (2013.01); *A61B 6/12* (2013.01); *A61B 7/00* (2013.01); *A61B 8/00* (2013.01); *A61N 1/0509* (2013.01); *A61N 1/0517* (2013.01)

(58) Field of Classification Search
USPC ................................................. 607/124, 133
See application file for complete search history.

(56) References Cited

U.S. PATENT DOCUMENTS

| 3,909,883 A | 10/1975 | Fegen |
| 4,414,986 A | 11/1983 | Dickhudt |

(Continued)

FOREIGN PATENT DOCUMENTS

| WO | 9853878 | 12/1998 |
| WO | 9903532 | 1/1999 |

(Continued)

OTHER PUBLICATIONS

Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.

(Continued)

*Primary Examiner* — Long V Le
*Assistant Examiner* — Farshad Negarestan
(74) *Attorney, Agent, or Firm* — Novel IP

(57) ABSTRACT

A method of implanting electrically conductive leads in the gastrointestinal musculature for stimulation of target tissues involves an endoscopic approach through the esophagus. An endoscope is inserted into the esophagus of a patient. The mucosal surface of the anterior esophagus is punctured in the region encompassing the lower esophageal sphincter (LES). A tunnel is created through the submucosa and exits at the muscularis propria, adventitia, or serosal side of the stomach. The lead is navigated further to the anterior abdominal wall. A first end of the lead remains within the gastrointestinal musculature while a second end of the lead is positioned just outside the anterior abdominal wall. The first end of the lead comprises at least one electrode. An implantable pulse generator (IPG) is implanted and operably connected to the second end of the lead to provide electrical stimulation to target tissues.

32 Claims, 5 Drawing Sheets

(51) Int. Cl.
  *A61B 6/12* (2006.01)
  *A61B 7/00* (2006.01)
  *A61B 8/00* (2006.01)
  *A61N 1/05* (2006.01)

(56) References Cited

U.S. PATENT DOCUMENTS

| | | |
|---|---|---|
| 4,612,934 A | 9/1986 | Borkan |
| 5,117,827 A | 6/1992 | Stuebe |
| 5,188,104 A | 2/1993 | Wernicke |
| 5,193,539 A | 3/1993 | Schulman |
| 5,197,491 A | 3/1993 | Anderson |
| 5,231,988 A | 8/1993 | Wernicke |
| 5,263,480 A | 11/1993 | Wernicke |
| 5,292,344 A | 3/1994 | Douglas |
| 5,423,872 A | 6/1995 | Cigaina |
| 5,540,730 A | 7/1996 | Terry |
| 5,556,425 A | 9/1996 | Hewson |
| 5,649,902 A | 7/1997 | Yoon |
| 5,690,691 A | 11/1997 | Chen |
| 5,716,385 A | 2/1998 | Mittal |
| 5,716,392 A | 2/1998 | Bourgeois |
| 5,836,994 A | 11/1998 | Bourgeois |
| 5,861,014 A | 1/1999 | Familoni |
| 5,861,044 A | 1/1999 | Crenshaw |
| 5,882,340 A | 3/1999 | Yoon |
| 5,935,126 A | 8/1999 | Riza |
| 5,995,872 A | 11/1999 | Bourgeois |
| 6,006,755 A | 12/1999 | Edwards |
| 6,026,326 A | 2/2000 | Bardy |
| 6,041,258 A | 3/2000 | Cigaina |
| 6,051,017 A | 4/2000 | Loeb |
| 6,091,992 A | 7/2000 | Bourgeois |
| 6,097,984 A | 8/2000 | Douglas |
| 6,216,039 B1 | 4/2001 | Bourgeois |
| 6,243,607 B1 | 6/2001 | Mintchev |
| 6,254,598 B1 | 7/2001 | Edwards |
| 6,285,897 B1 | 9/2001 | Kilcoyne |
| 6,321,124 B1 | 11/2001 | Cigaina |
| 6,381,495 B1 | 4/2002 | Jenkins |
| 6,449,511 B1 | 9/2002 | Mintchev |
| 6,510,332 B1 | 1/2003 | Greenstein |
| 6,542,776 B1 | 4/2003 | Gordon |
| 6,571,127 B1 | 5/2003 | Ben-Haim |
| 6,587,719 B1 | 7/2003 | Barrett |
| 6,591,137 B1 | 7/2003 | Fischell |
| 6,611,715 B1 | 8/2003 | Boveja |
| 6,615,084 B1 | 9/2003 | Cigaina |
| 6,678,561 B2 | 1/2004 | Forsell |
| 6,684,104 B2 | 1/2004 | Gordon |
| 6,749,607 B2 | 6/2004 | Edwards |
| 6,754,536 B2 | 6/2004 | Swoyer |
| 6,760,626 B1 | 7/2004 | Boveja |
| 6,826,428 B1 | 11/2004 | Chen |
| 6,832,114 B1 | 12/2004 | Whitehurst |
| 6,853,862 B1 | 2/2005 | Marchal |
| 6,879,859 B1 | 4/2005 | Boveja |
| 6,901,295 B2 | 5/2005 | Sharma |
| 6,947,792 B2 | 9/2005 | Ben-Haim |
| 7,006,871 B1 | 2/2006 | Darvish |
| 7,016,735 B2 | 3/2006 | Imran |
| 7,054,689 B1 | 5/2006 | Whitehurst |
| 7,054,690 B2 | 5/2006 | Imran |
| 7,076,305 B2 | 7/2006 | Imran |
| 7,076,306 B2 | 7/2006 | Marchal |
| 7,087,053 B2 | 8/2006 | Vanney |
| 7,114,502 B2 | 10/2006 | Schulman |
| 7,120,498 B2 | 10/2006 | Imran |
| 7,146,216 B2 | 12/2006 | Bumm |
| 7,167,750 B2 | 1/2007 | Knudson |
| 7,177,693 B2 | 2/2007 | Starkebaum |
| 7,200,443 B2 | 4/2007 | Faul |
| 7,203,551 B2 | 4/2007 | Houben |
| 7,263,405 B2 | 8/2007 | Boveja |
| 7,299,091 B2 | 11/2007 | Barrett |
| 7,310,557 B2 | 12/2007 | Maschino |
| 7,340,306 B2 | 3/2008 | Barrett |
| 7,343,201 B2 | 3/2008 | Mintchev |
| 7,363,084 B2 | 4/2008 | Kurokawa |
| 7,444,183 B2 | 10/2008 | Knudson |
| 7,477,994 B2 | 1/2009 | Sunshine |
| 7,519,431 B2 | 4/2009 | Goetz |
| 7,599,736 B2 | 10/2009 | DiLorenzo |
| 7,620,454 B2 | 11/2009 | Dinsmoor |
| 7,676,270 B2 | 3/2010 | Imran |
| 7,702,394 B2 | 4/2010 | Imran |
| 7,702,395 B2 | 4/2010 | Towe |
| 7,711,437 B1 | 5/2010 | Bornzin |
| 7,720,539 B2 | 5/2010 | Mintchev |
| 7,729,771 B2 | 6/2010 | Knudson |
| 7,734,355 B2 | 6/2010 | Cohen |
| 7,738,961 B2 | 6/2010 | Sharma |
| 7,742,818 B2 | 6/2010 | Dinsmoor |
| 7,794,425 B2 | 9/2010 | Gobel |
| 7,835,796 B2 | 11/2010 | Maschino |
| 7,899,540 B2 | 3/2011 | Maschino |
| 7,914,468 B2 | 3/2011 | Shalon |
| 7,962,214 B2 | 6/2011 | Byerman |
| 8,160,709 B2 | 4/2012 | Soffer |
| 8,282,561 B2 | 10/2012 | Towe |
| 8,447,403 B2 | 5/2013 | Sharma |
| 8,447,404 B2 | 5/2013 | Sharma |
| 8,452,407 B2 | 5/2013 | Whitehurst |
| 8,467,874 B2 | 6/2013 | Chen |
| 8,467,884 B2 | 6/2013 | Chen |
| 8,543,210 B2 | 9/2013 | Sharma |
| 8,594,811 B2 | 11/2013 | Chen |
| 8,712,529 B2 | 4/2014 | Sharma |
| 8,712,530 B2 | 4/2014 | Sharma |
| 8,761,903 B2 | 6/2014 | Chen |
| 2001/0041831 A1 | 11/2001 | Starkweather |
| 2002/0161414 A1 | 10/2002 | Flesler |
| 2002/0165589 A1 | 11/2002 | Imran |
| 2003/0014086 A1 | 1/2003 | Sharma |
| 2003/0055463 A1 | 3/2003 | Gordon |
| 2003/0078633 A1 | 4/2003 | Firlik |
| 2003/0144708 A1 | 7/2003 | Starkebaum |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0116977 A1 | 6/2004 | Finch |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0251219 A1 | 11/2005 | Evans |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0167498 A1 | 7/2006 | DiLorenzo |
| 2006/0206160 A1 | 9/2006 | Cigaina |
| 2006/0218011 A1 | 9/2006 | Walker |
| 2006/0247722 A1 | 11/2006 | Maschino |

(56) References Cited

U.S. PATENT DOCUMENTS

| | | |
|---|---|---|
| 2006/0265021 A1 | 11/2006 | Herbert |
| 2007/0016274 A1 | 1/2007 | Boveja |
| 2007/0049793 A1 | 3/2007 | Ignagni |
| 2007/0106337 A1 | 5/2007 | Errico |
| 2007/0162084 A1 | 7/2007 | Chen |
| 2007/0162085 A1 | 7/2007 | DiLorenzo |
| 2007/0238942 A1 | 10/2007 | Baylor |
| 2007/0239248 A1 | 10/2007 | Hastings |
| 2008/0021512 A1 | 1/2008 | Knudson |
| 2008/0039904 A1 | 2/2008 | Bulkes |
| 2008/0086179 A1 | 4/2008 | Sharma |
| 2008/0147137 A1 | 6/2008 | Cohen |
| 2008/0154191 A1 | 6/2008 | Gobel |
| 2008/0195171 A1 | 8/2008 | Sharma |
| 2008/0208355 A1* | 8/2008 | Stack et al. ............... 623/23.65 |
| 2009/0020406 A1 | 1/2009 | Nirmalakhandan |
| 2009/0030475 A1* | 1/2009 | Brynelsen et al. ............ 607/40 |
| 2009/0069803 A1 | 3/2009 | Starkebaum |
| 2009/0132001 A1 | 5/2009 | Soffer |
| 2009/0204063 A1 | 8/2009 | Policker |
| 2009/0264951 A1* | 10/2009 | Sharma ......................... 607/40 |
| 2009/0281553 A1* | 11/2009 | Kalloo et al. ................ 606/129 |
| 2010/0198039 A1 | 8/2010 | Towe |
| 2010/0324432 A1 | 12/2010 | Bjoerling |
| 2011/0004266 A1 | 1/2011 | Sharma |
| 2011/0071589 A1 | 3/2011 | Starkebaum |
| 2011/0295335 A1 | 12/2011 | Sharma |
| 2011/0295336 A1 | 12/2011 | Sharma |
| 2011/0307027 A1 | 12/2011 | Sharma |
| 2011/0307028 A1 | 12/2011 | Sharma |
| 2012/0232610 A1 | 9/2012 | Soffer |
| 2012/0265103 A1 | 10/2012 | Policker |
| 2013/0035740 A1 | 2/2013 | Sharma |
| 2013/0090551 A1 | 4/2013 | Sharma |
| 2013/0178912 A1 | 7/2013 | Sharma |
| 2013/0231660 A1 | 9/2013 | Edwards |
| 2014/0018657 A1 | 1/2014 | Sharma |
| 2014/0088664 A1 | 3/2014 | Sharma |

FOREIGN PATENT DOCUMENTS

| | | |
|---|---|---|
| WO | 9930776 | 6/1999 |
| WO | 0061223 | 10/2000 |
| WO | 0061223 A1 | 10/2000 |
| WO | 0061224 | 10/2000 |
| WO | 0061224 A1 | 10/2000 |
| WO | 0243467 | 6/2002 |
| WO | 0243467 A2 | 6/2002 |
| WO | 02089655 | 11/2002 |
| WO | 2005051486 A1 | 9/2005 |
| WO | 2007137026 | 11/2007 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |

OTHER PUBLICATIONS

Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.

Cigaina, Valerio; Long-term Follow-Up of Gastric Stimulation for Obesity: The Mestre 8-Year Experience; Obesity Surgery; 14; 2004; S14-22.

Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.

Sanmiguel et al, 'Effect of electrical stimulation of the LES on LES pressure in a canine model'; Am J Physiol Gastrointest Live Physiol; 295: 389-394; 2008.

Clarke et al,. 'An Endoscopic Implantable Device Stimulates the LES On-Demand by Remote Control in a Canine Model'; Gastrointestinal Endoscopy, vol. 63, No. 5; 2006, AB103, 759.

Kantsevoy et al., 'An Endoscopically Implantable On-Demand Stimulator Is Successful in Increasing Lower Esophageal Sphincter Pressure in a Porcine Model': Gastrointestinal Endoscopy, vol. 61, No. 5: 2005, AB79, 222.

Notice of Allowance dated Jul. 21, 2014 for U.S. Appl. No. 13/447,168.

Notice of Allowance dated Apr. 3, 2014 for U.S. Appl. No. 13/447,168.

Notice of Allowance dated Mar. 17, 2014 for U.S. Appl. No. 13/447,168.

Office Action dated Jul. 8, 2014 for U.S. Appl. No. 13/463,803.

Shellock, Frank G. 'RF Bion Microstimulator' MRISafety.com, http://www.mrisafety.com/Safetylnfov.asp?SafetylnfolD=254, Shellock R & D Services, Inc. and Frank G. Shellock, Ph.D., 4 pages, 2014.

Christensen et al., 'Physiologic Specialization at Esophagogastric Junction in Three Species' , American Journal of Physiology, vol. 225, No. 6, Dec. 1973, 1265-1270.

Ellis, et al., 'The Prevention of Experimentally Induced Reflux by Electrical Stimulation of the Distal Esophagus', American Journal of Surgery, vol. 115, Apr. 1968, 482-487.

Gonzalez et al., 'Different Responsiveness of Excitatory and Inhibitory Enteric Motor Neurons in the Human Esophagus to Electrical Field Stimulation and to Nicotine' , Am J Physiol Gastrointest Liver Physiol, 287:G299-G306, 2004.

Kahrilas et al., 'Impact of Fundoplication on Bolus Transit Across Esophagogastric Junction' , American Physiological Society, 1998, 1386-1393.

Kamath et al., 'Neurocardiac and Cerebral Responses Evoked by Esophageal Vago-Afferent Stimulation in Humans: Effects of Varying Intensities' , Cardiovascular Research, 40 (1998) 591-599.

Lund et al., 'Electrical Stimulation of Esophageal Smooth Muscle and Effects of Antagonists' , American Journal of Physiology, vol. 217, No. 5, Nov. 1969, 1369-1374.

Stein et al., 'Three-dimensional Imaging of the Lower Esophageal Sphincter in Gastroesophageal Reflux Disease,' Annual Meeting of the American Surgical Association, Apr. 11-13, 1991, 374-383.

International Search Report for PCT/US2007/068907, Aug. 7, 2008.

International Search Report for PCT/US2012/036408, Aug. 17, 2012.

Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.

International Search Report for PCT/US2008/053780, Jun. 8, 2009.

International Search Report for PCT/US2008/056479, Aug. 20, 2008.

International Search Report for PCT/US2011/027243, Jul. 8, 2011.

International Search Report for PCT/US12/053576, Dec. 24, 2012.

International Search Report for PCT/US2012/033695, Aug. 7, 2012.

EPO Search Report EP09704463, Jan. 10, 2011, Virender K. Sharma.

International Search Report for PCT/US2013/056520, Apr. 4, 2014.

Clarke et al., 'An endoscopically implantable device stimulates the lower esophageal sphincter on demand by remote control: a study using a canine model', Endoscopy 2007; 39: 72-76.

Xing et al., 'Gastric Electrical Stimulation Significantly Increases Canine Lower Esophageal Pressure' M1811 Cleveland, OH, 2005.

Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.

* cited by examiner

ENDOSCOPIC LEAD IMPLANTATION METHOD

CROSS REFERENCE

The present application relies on U.S. Provisional Application No. 61/530,781, filed on Sep. 2, 2011, entitled "Endoscopic Lead Implantation Method", which is incorporated herein by reference.

FIELD

The present specification relates generally to the improved implantation of electrically conductive leads within a patient to provide electrical stimulation to target tissues and thereby provide therapy for a multitude of disorders, including obesity and gastroesophageal reflux disease (GERD). More particularly, the present specification relates to an improved method of electrically conductive lead implantation utilizing an endoscopic approach through the esophagus.

BACKGROUND

Obesity is a common condition and a major public health problem in developed nations including the United States of America. As of 2009, more than two thirds of American adults, approximately 127 million people, were either overweight or obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States approximately $100 billion annually in direct and indirect health care expenses and in lost productivity. This trend is also apparent in many other developed countries.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m$^2$ is associated with significant co-morbidities. Morbid obesity is defined as possessing either a body weight more than 100 pounds greater than ideal or a body mass index (BMI) greater than 40 kg/m$^2$. Approximately 5% of the U.S. population meets at least one of the criteria for morbid obesity. Morbid obesity is associated with many diseases and disorders including, for example: diabetes; hypertension; heart attacks; strokes; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are also associated with morbid obesity. Taken together, the diseases associated with morbid obesity markedly reduce the odds of attaining an average lifespan. The sequelae raise annual mortality in affected people by a factor of 10 or more.

Current treatments for obesity include diet, exercise, behavioral treatments, medications, surgery (open and laparoscopic) and endoscopic devices. New drug treatments for obesity are currently being evaluated in clinical trials. However, a high efficacy pharmaceutical treatment has not yet been developed. Further, short-term and long-term side effects of pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include lap band surgery or gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive surgery with a malabsorptive procedure. Typical malabsorptive procedures divide small intestinal flow into a biliary-pancreatic conduit and a food conduit. Potential long-term complications associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopically placed gastric balloons restrict gastric volume and result in satiety with smaller meals. Endoscopic procedures and devices to produce gastric pouch and gastrojejunal anastomosis to replicate laparoscopic procedures are also in development. These procedures, however, are not without risks.

Gastro-esophageal reflux disease (GERD) is another common health problem and is expensive to manage in both primary and secondary care settings. This condition results from exposure of esophageal mucosa to gastric acid as the acid refluxes from the stomach into the esophagus. The acid damages the esophageal mucosa resulting in heartburn, ulcers, bleeding, and scarring, and long term complications such as Barrett's esophagus (pre-cancerous esophageal lining) and adeno-cancer of the esophagus.

Lifestyle advice and antacid therapy are advocated as first line treatment for the disease. However, since most patients with moderate to severe cases of GERD do not respond adequately to these first-line measures and need further treatment, other alternatives including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastro-esophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in nonpharmacological options for managing their reflux disease.

Several endoscopic procedures for the treatment of GERD have been tried. These procedures can be divided into three approaches: endoscopic suturing wherein stitches are inserted in the gastric cardia to plicate and strengthen the lower esophageal sphincter, endoscopic application of energy to the lower esophagus, and injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures are associated with significant morbidity and small but not insignificant mortality rates. Moreover, long-term follow-up with patients treated by surgery suggests that many patients continue to need acid suppressive medication. There is also no convincing evidence that fundoplication reduces the risk of esophageal adenocarcinoma in the long term.

Gastric electrical stimulation (GES) is another therapy aimed at treating both obesity and GERD. GES employs an implantable, pacemaker-like device to deliver low-level electrical stimulation to the gastrointestinal tract. For obesity, GES operates by disrupting the motility cycle and/or stimulating the enteric nervous system, thereby increasing the duration of satiety experienced by the patient. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Abiliti® implantable gastric stimulation device, manufactured by IntraPace, is currently available in Europe for treatment of obesity.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis, including nausea and vomiting.

Electrical stimulation has also been suggested for use in the treatment of GERD, wherein the stimulation is supplied to the lower esophageal sphincter (LES). For example, in U.S. Pat. No. 6,901,295, assigned to Endostim, Inc., "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety.

Similarly, U.S. Pat. No. 6,097,984, which is incorporated by reference in its entirety, discloses "a system and method for directly stimulating the LES of a patient in order to normally maintain it in a closed state, thereby preventing reflux and treating the symptoms of GERD. The stimulation is inhibited in response to patient swallowing, by monitoring esophageal motility and timing out an inhibition period following detection of motility representative of swallowing. The system utilizes an implanted stimulator which is programmed to deliver a train of stimulus pulses to one or more electrodes fixed around the gastro-esophageal junction and connected to the stimulator by one or more leads. The motility sensing is done by a sensor for sensing mechanical wave movement or electrical signals representative of high motility following swallowing. The motility sensor and stimulating electrodes are attached laparoscopically, and are preferably carried by a common stent carrier which is sutured around the lower esophagus." In this application, the LES is stimulated to constantly be in a closed state and instantaneously opened when swallowing is detected.

Typically, the leads for GES are implanted in the gastrointestinal wall using a laparoscopic approach. The gastrointestinal musculature is entered through the serosal surface of the stomach. Unfortunately, the use of laparoscopy is not without its risks and is contraindicated in some patients, such as individuals who have adhesions from previous abdominal surgeries. Though it is less invasive than open surgery, laparoscopy still involves tissue incisions for the introduction of the trocars. These incision sites must be sutured closed after the procedure and represent possible infection points. In addition, trocar placement runs the risk of injuring blood vessels, the large bowel, or other organs. Laparoscopy also includes the inherent risk of being converted to open surgery should complications arise during the procedure. Therefore, a need exists for implanting electrical leads in the gastrointestinal tract wall of a patient that is less invasive than current modalities and for those patients for whom laparoscopy is not an option. In addition, laparoscopy is more costly, time consuming, and requires a greater period of patient recovery than less invasive approaches. Therefore, a need exists for a method of implanting electrical leads in the gastrointestinal tract wall of a patient that is also quicker and more cost-effective with less time required for patient healing.

SUMMARY

The present specification is directed toward a method of implanting electrically conductive leads in the gastrointestinal musculature utilizing an endoscopic approach, comprising: a) inserting an endoscope into an esophagus of a patient; b) identifying a lower esophageal sphincter (LES); c) entering a gastrointestinal (GI) wall, with a lead, from a mucosal side by puncturing a mucosa of an anterior segment of a region encompassing the LES; d) creating a tunnel in a submucosa of the anterior segment of the region encompassing the LES; e) exiting the GI wall through a muscularis propria, adventitia, or serosal side of the stomach; f) navigating the lead to an anterior abdominal wall; and g) exiting a second end of the lead through the anterior abdominal wall while leaving a first end in the gastrointestinal musculature, wherein the region encompassing the LES comprises an area 3 cm above and 3 cm below the LES.

In one embodiment, the tunnel created in the submucosa of the anterior segment of the LES is less than 5 cm in length. In another embodiment, the tunnel created in the submucosa of the anterior segment of the LES is within the range of 1 cm to 5 cm in length.

In one embodiment, the first end of said lead is not anchored to a gastrointestinal tissue. In another embodiment, the first end of said lead is anchored to a gastrointestinal tissue.

In one embodiment, the leads are adapted to electrically stimulate the gastrointestinal musculature in a therapeutically effective amount to treat any one or combination of obesity and gastroesophageal reflux disease (GERD).

In one embodiment, the method of implanting electrically conductive leads in the gastrointestinal musculature utilizing an endoscopic approach further comprises using magnetic, ultrasound, radiologic, or fluoroscopic imaging, or physical indicators, mechanical indicators, or auditory indicators, in addition to visual imaging to assist in lead navigation.

In one embodiment, the method of implanting electrically conductive leads in the gastrointestinal musculature utilizing an endoscopic approach further comprises subcutaneously implanting an implantable pulse generator (IPG) proximate the lead exit point in the anterior abdominal wall. In one embodiment, the second end of said lead is attached with said IPG so that said lead can receive pulse signals from said IPG. In another embodiment, wireless communication is used to transmit pulse signals from said IPG to said lead.

The present specification is also directed toward a method of implanting electrically conductive leads in the gastrointestinal musculature utilizing an endoscopic approach, comprising: a) inserting an endoscope into the esophagus of a patient; b) identifying the lower esophageal sphincter (LES); c) entering the gastrointestinal (GI) wall with a lead from the mucosal side by puncturing the mucosa of the anterior segment of a region encompassing the LES; d) creating a tunnel in the submucosa of the anterior segment of the region encompassing the LES; e) exiting the GI wall through the serosal side of the stomach; f) navigating the lead to the anterior abdominal wall; and, g) exiting a second end of the lead through the anterior abdominal wall while leaving a first end in the gastrointestinal musculature, wherein the region encompassing the LES comprises an area 3 cm above and 3 cm below the LES.

In one embodiment, the tunnel created in the submucosa of the anterior segment of the LES is equal to or greater than 5 cm in length.

In one embodiment, the first end of said lead is not anchored to a gastrointestinal tissue. In another embodiment, the first end of said lead is anchored to a gastrointestinal tissue.

In one embodiment, the method of implanting electrically conductive leads in the gastrointestinal musculature utilizing an endoscopic approach further comprises the step of insufflating the stomach. In one embodiment, the method further comprises the steps of: a) finding a site where the stomach is in cross-approximation with the anterior abdominal wall; b) securing the stomach with one or more anchors; c) exiting the serosal surface of the stomach proximate said site; and d) entering the anterior abdominal wall proximate said site.

In one embodiment, the leads are used to electrically stimulate the gastrointestinal musculature in an effort to treat any one or combination of obesity and gastroesophageal reflux disease (GERD).

In one embodiment, the method of implanting electrically conductive leads in the gastrointestinal musculature utilizing an endoscopic approach further comprises using magnetic, ultrasound, radiologic, or fluoroscopic imaging, or physical indicators, mechanical indicators, or auditory indicators, in addition to visual imaging to assist in lead navigation.

In one embodiment, the method of implanting electrically conductive leads in the gastrointestinal musculature utilizing an endoscopic approach further comprises subcutaneously implanting an implantable pulse generator (IPG) proximate the lead exit point in the anterior abdominal wall. In one embodiment, the second end of said lead is attached with said IPG so that said lead can receive pulse signals from said IPG. In another embodiment, wireless communication is used to transmit pulse signals from said IPG to said lead.

The present specification is also directed toward a method of implanting electrically conductive leads in the gastrointestinal musculature utilizing an endoscopic approach, comprising: a) inserting an endoscope into an esophagus of a patient; b) advancing said endoscope to a desired implantation site along a gastrointestinal tract of said patient; c) entering a gastrointestinal (GI) wall with a lead from a mucosal side by puncturing a mucosa of an anterior segment of said desired implantation site; d) creating a tunnel in the submucosa of the anterior segment of said desired implantation site; e) exiting the GI wall through a muscularis propria, adventitia, or serosal side of said desired implantation site; f) navigating a second end of said lead to a predetermined endpoint within an abdomen of said patient; and g) leaving a first end of said lead in the gastrointestinal musculature at said desired implantation site.

In one embodiment, said predetermined endpoint is within a peritoneal cavity of said patient. In another embodiment, the method of implanting electrically conductive leads in the gastrointestinal musculature utilizing an endoscopic approach further comprises the step of navigating said second end of said lead through an anterior abdominal wall of said patient and wherein said predetermined endpoint is within the subcutaneous region of the abdomen.

In one embodiment, the leads are used to electrically stimulate the gastrointestinal musculature in an effort to treat a condition of a gastrointestinal system of said patient.

In one embodiment, the method of implanting electrically conductive leads in the gastrointestinal musculature utilizing an endoscopic approach further comprises implanting an implantable pulse generator (IPG) proximate said predetermined endpoint. In one embodiment, the second end of said lead is attached with said IPG so that said lead can receive pulse signals from said IPG. In another embodiment, wireless communication is used to transmit pulse signals from said IPG to said lead.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings.

DETAILED DESCRIPTION

Figure 1:
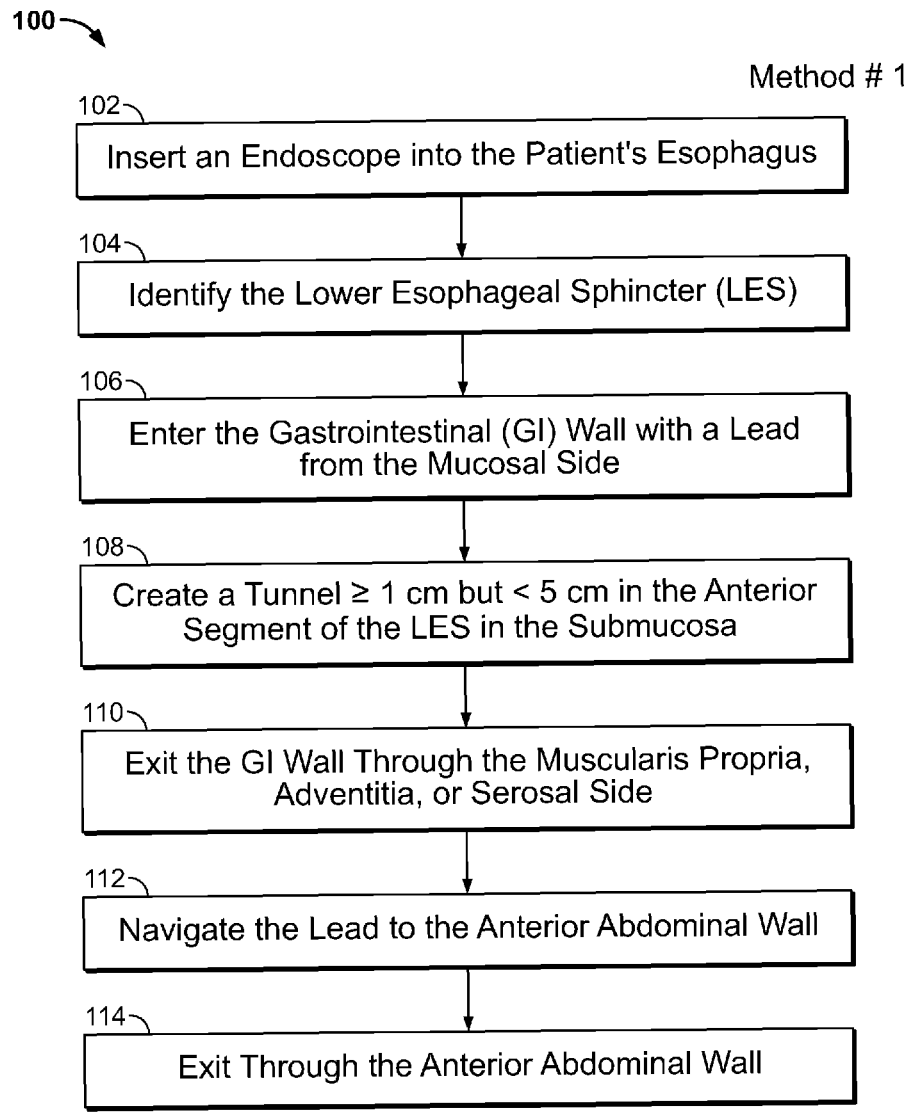
FIG. 1 is a flow chart listing the steps involved in a first method of endoscopic lead implantation in accordance with one embodiment of the present specification.

The present specification is directed toward a method of implanting electrically conductive leads in the gastrointestinal musculature utilizing an endoscopic approach. An endoscopic approach involves entering the gastrointestinal wall from the mucosal side rather than entering from the serosal side, which is involved with a laparoscopic approach. The leads are used to provide electrical stimulation to the gastrointestinal musculature in an effort to treat a variety of gastrointestinal disorders, such as, obesity.

In one embodiment, the endoscopic approach of implanting leads in the gastrointestinal musculature includes the following steps. An endoscope is inserted into a patient's esophagus and is advanced until the lower esophageal sphincter (LES) is identified. At this point, or within +/−3 cm from the LES, the gastrointestinal wall is entered from the mucosal side by creating a tunnel through the submucosa of the anterior segment of the LES. An appropriately designed catheter is used to bore the tunnel and implant the lead. The catheter can have mechanisms to assist in guidance such as a magnet, camera, ultrasound transducer, and the like. One of ordinary skill in the art would know what features a conventional catheter would preferably have to most effectively assist in the execution of the methods disclosed herein.

The tunnel is continued for a predetermined distance and then exits through the muscularis propria, adventitia, or serosal side of the gastrointestinal wall. From this point, the catheter is used to navigate the lead to the anterior abdominal wall where an exit point is created. Once implanted, the lead is positioned so that a first end lies within the gastrointestinal musculature, anchored or not, while a second end exits through the anterior abdominal wall and continues subcutaneously until it reaches the implant location. The first end comprises at least one electrode to be used for electrical stimulation of the target tissues. In one embodiment, the second end is operably connected to an implantable pulse generator.

In another embodiment, the endoscopic approach of implanting leads in the gastrointestinal musculature includes the steps listed above plus the following optional steps. The stomach is insufflated to assist in lead implantation. A site is located where the stomach is in cross-approximation with the anterior abdominal wall. The stomach is then secured with one or more anchors to prevent it from moving during the implantation process. The lead is then tunneled through the gastrointestinal musculature, exiting the stomach from the serosal surface and entering the anterior abdominal wall at the site located above. The lead then exits through the anterior abdominal wall as described in the previous embodiment.

In another embodiment, the endoscopic approach of implanting leads in the gastrointestinal musculature can be used to implant leads anywhere in the gastrointestinal tract and comprises the following steps. An endoscope is inserted into an esophagus of a patient. The endoscope is advanced to a desired implantation site along the gastrointestinal tract of the patient. The gastrointestinal (GI) wall is entered with a lead from the mucosal side by puncturing the mucosa of an anterior segment of the desired implantation site. A tunnel is created in the submucosa of the anterior segment of the desired implantation site. The GI wall is exited through the muscularis propria, adventitia, or serosal side of the desired implantation site. A second end of the lead is navigated to a predetermined endpoint within the abdomen of the patient. The first end of the lead is left in the gastrointestinal musculature at the desired implantation site, which may or may not be anchored. The first end comprises at least one electrode to be used for electrical stimulation of the target tissues. In one embodiment, the second end is operably connected to an implantable pulse generator (IPG).

In one embodiment, after lead implantation, a pulse generator is implanted proximate the lead exit point or endpoint in the abdomen. In one embodiment, the pulse generator is implanted subcutaneously. In another embodiment, the pulse generator is implanted within the peritoneal cavity. The pulse generator transmits impulses to the implanted electrode which in turn supplies electrical stimulation to the gastrointestinal musculature. In one embodiment, the lead is physically connected to the IPG with a wired connection via a metal-to-metal contact at the proximal end. In another embodiment, the IPG communicates wirelessly with the lead. The distal end of the lead is provided with electrodes which are positioned in the gastrointestinal musculature. In one embodiment the electrodes are left within the musculature without any anchoring means. In another embodiment, the electrodes are anchored to the musculature using sutures or similar structures.

In various embodiments, proper positioning of the lead is ensured through the use of magnetic, ultrasound, radiologic, or fluoroscopic imaging, or other physical, mechanical, or auditory indicators, in addition to visual observation.

The present specification is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is a flow chart 100 listing the steps involved in a first method of endoscopic lead implantation in accordance with one embodiment of the present specification. In the first step 102, an endoscope is inserted into the esophagus of a patient who is to receive therapy involving electrical stimulation to the gastrointestinal musculature. The endoscope is advanced until the physician is able to identify the lower esophageal sphincter (LES) 104. At this point, the physician uses a catheter to puncture the mucosa of the gastrointestinal wall at the LES 106. A tunnel is then bored in the submucosa of the anterior segment of the LES 108. In one embodiment, the length of the tunnel is greater than or equal to 1 cm but less than 5 cm.

A first end of the lead remains within the tunnel created in the gastrointestinal wall. In one embodiment, the first end comprises at least one electrode to be used for electrical stimulation of the target tissues. After boring the tunnel, the physician then directs the lead through the remainder of the gastrointestinal wall, exiting through the muscularis propria, adventitia, or serosal side 110. Once through the entire thickness of the gastrointestinal wall, the lead is navigated to the anterior abdominal wall 112. The physician then creates an exit point and directs a second end of the lead through the anterior abdominal wall 114. When the lead has been placed in its operative position, the first end engages the gastrointestinal musculature while the second end exits through the anterior abdominal wall.

Figure 2:
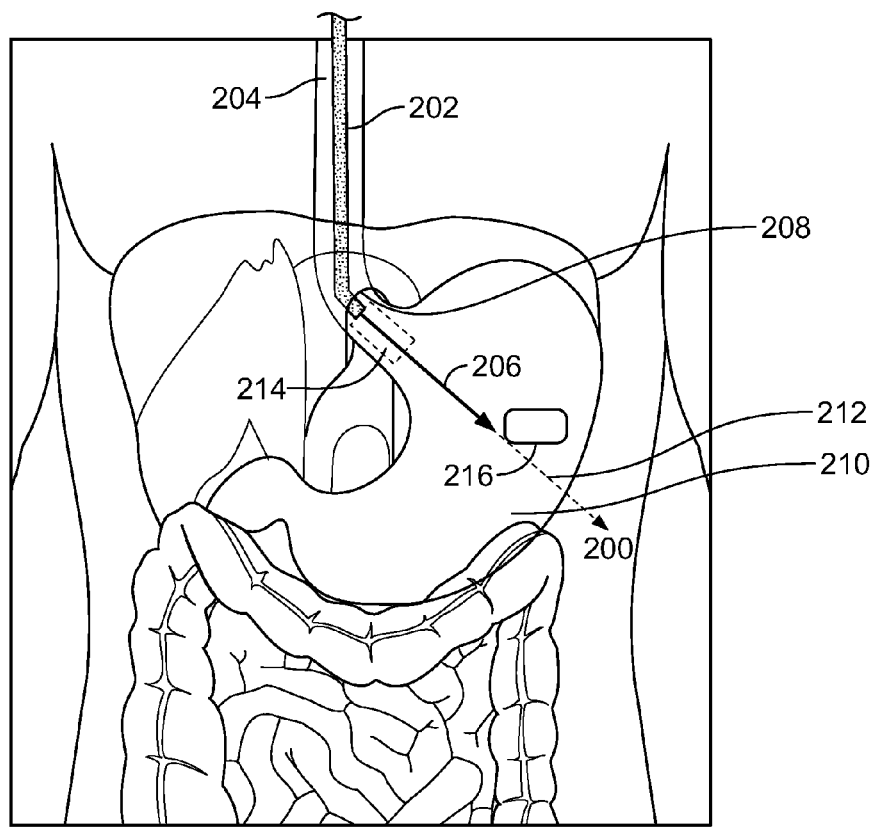
FIG. 2 is an illustration of a patient's abdominal viscera depicting the lead implantation pathway of the first implantation method described in the flow chart of FIG. 1.

FIG. 2 is an illustration of a patient's abdominal viscera depicting the lead implantation pathway 200 of the first implantation method described in the flow chart of FIG. 1. An endoscope 202 is depicted in the esophagus 204 of the patient. The distal end of the endoscope 202 is positioned proximate the LES 208. A submucosal tunnel 214 is bored through the anterior segment of the LES 208 and the anterior cardiac portion of the stomach 210. As discussed above, in one embodiment of the first method, the submucosal tunnel 214 is greater than or equal to 1 cm but less than 5 cm in length.

A first end of the lead 206, comprising at least one electrode, remains in the gastrointestinal musculature. A second end, opposite said first end, of the endoscopically implanted lead 206 exits the tunnel 214 in the gastrointestinal wall through the serosal surface of the stomach 210. The second end of the lead 206 then passes through the anterior abdominal wall, resulting in lead exteriorization 212. A subcutaneously implanted IPG 216 is depicted proximate the lead exit point in the anterior abdominal wall. The IPG transmits impulses to the implanted electrode to effectuate electrical stimulation of the gastrointestinal musculature.

Figure 3:
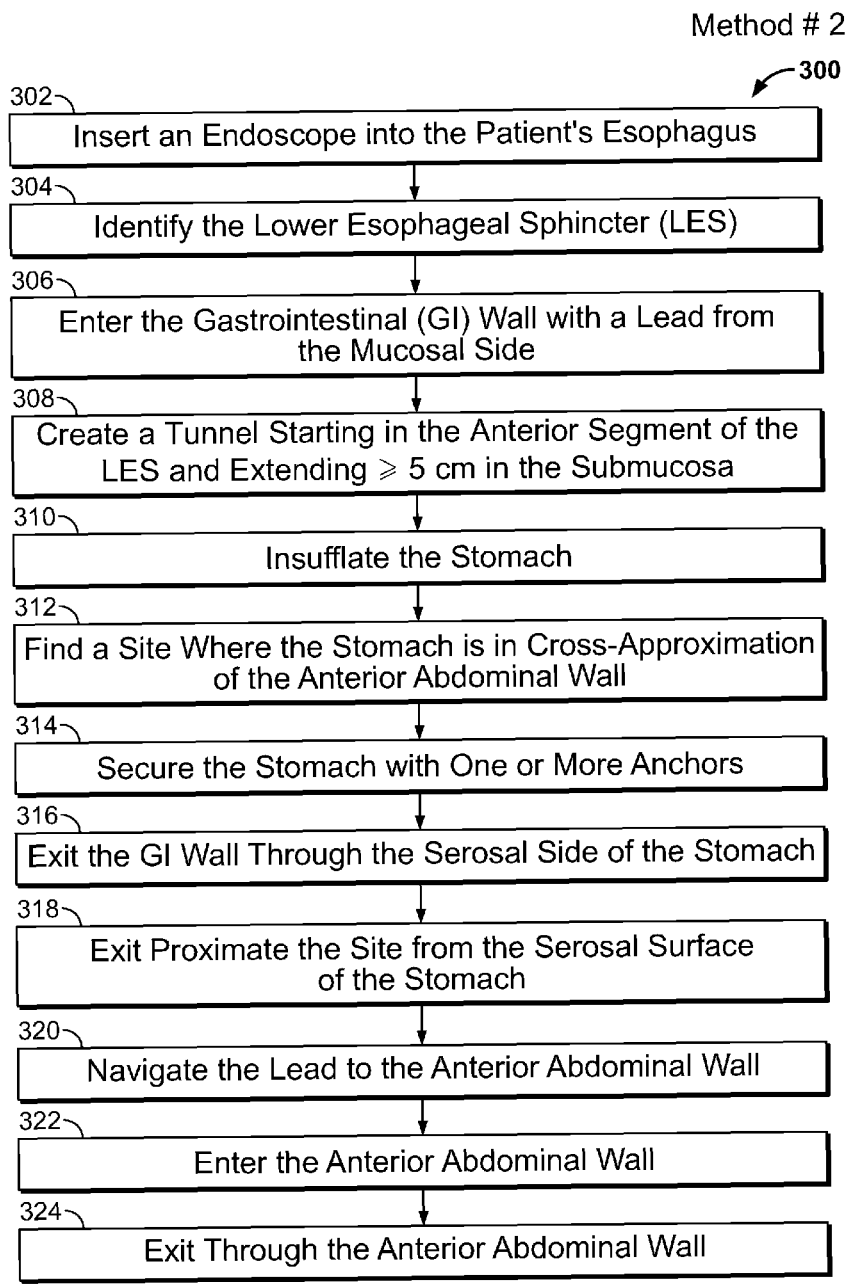
FIG. 3 is a flow chart listing the steps involved in a second method of endoscopic lead implantation in accordance with one embodiment of the present specification.

FIG. 3 is a flow chart 300 listing the steps involved in a second method of endoscopic lead implantation in accordance with one embodiment of the present specification. This second method is similar to the first method discussed above, differing, however, in the length of the submucosal tunnel and the inclusion of certain additional steps.

In the first step 302, an endoscope is inserted into the esophagus of a patient who is to receive therapy involving electrical stimulation to the gastrointestinal musculature. The endoscope is advanced until the physician is able to identify the lower esophageal sphincter (LES) 304. At this point, the physician uses a specialized catheter to puncture the mucosa of the gastrointestinal wall at the LES 306. A tunnel is then bored in the submucosa of the anterior segment of the LES 308. In one embodiment, the length of the tunnel is greater than or equal to 5 cm. A first end of the lead remains within the tunnel created in the gastrointestinal wall. The first end comprises at least one electrode to be used for electrical stimulation of the target tissues.

The stomach is insufflated to facilitate the creation of the tunnel 310. A site is found and noted where the stomach is in cross-approximation with the anterior abdominal wall 312. The stomach is then secured with one or more anchors to prevent movement 314. The physician then directs the lead through the remainder of the gastrointestinal wall, exiting through the muscularis propria, adventitia, or serosal side 316. The exit point is proximate the site located above 318. The physician then navigates the lead to the anterior abdominal wall 320 proximate this same site. The lead then enters 322 and exits 324 the anterior abdominal wall. When the lead has been placed in its operative position, the first end engages the gastrointestinal musculature while the second end exits through the anterior abdominal wall.

Figure 4:
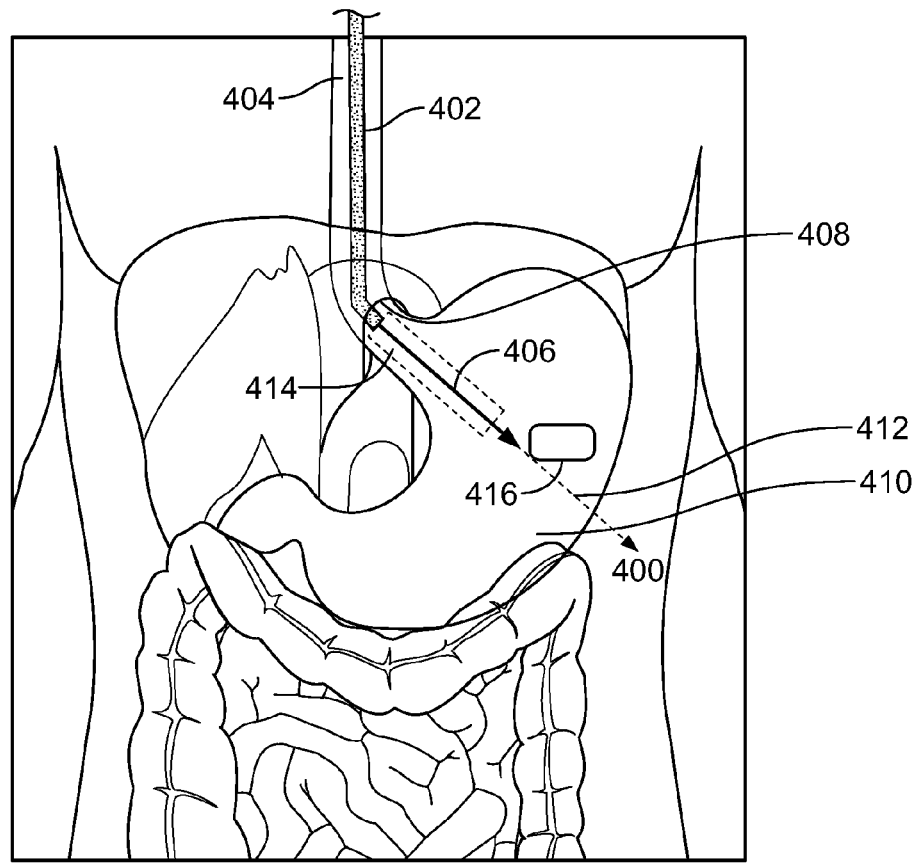
FIG. 4 is an illustration of a patient's abdominal viscera depicting the lead implantation pathway of the second implantation method described in the flow chart of FIG. 3; and, FIG. 5 is a flow chart listing the steps involved in a third method of endoscopic lead implantation in accordance with one embodiment of the present specification.

FIG. 4 is an illustration of a patient's abdominal viscera depicting the lead implantation pathway 400 of the second implantation method described in the flow chart of FIG. 3. An endoscope 402 is depicted in the esophagus 404 of the patient. The distal end of the endoscope 402 is positioned proximate the LES 408. A submucosal tunnel 414 has been bored through the anterior segment of the LES 408, the anterior cardiac portion of the stomach 410, and the anterior body portion of the stomach 410. As discussed above, in one embodiment of the second method, the submucosal tunnel 414 is greater than 5 cm in length.

A first end of the lead 406, comprising at least one electrode, remains in the gastrointestinal musculature. A second end, opposite said first end, of the endoscopically implanted lead 406 exits the tunnel 414 in the gastrointestinal wall through the serosal surface of the stomach 410. The second end of the lead 406 then passes through the anterior abdominal wall, resulting in lead exteriorization 412. A subcutaneously implanted IPG 416 is depicted proximate the lead exit point in the anterior abdominal wall. The IPG transmits impulses to the implanted electrode to effectuate electrical stimulation of the gastrointestinal musculature.

Figure 5:
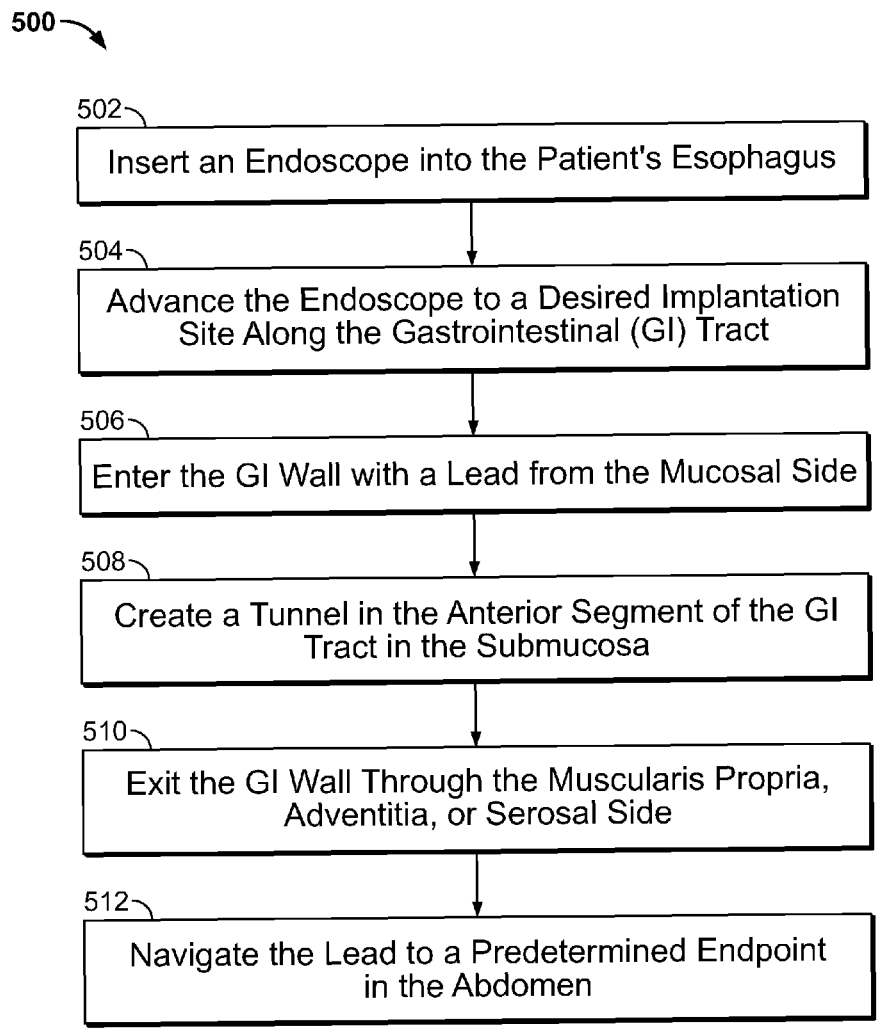

FIG. 5 is a flow chart 500 listing the steps involved in a third method of endoscopic lead implantation in accordance with one embodiment of the present specification. In the first step 502, an endoscope is inserted into the esophagus of a patient who is to receive therapy involving electrical stimulation to the gastrointestinal musculature. The endoscope is advanced to a desired implantation site along the gastrointestinal tract of the patient 504. At this point, the physician uses a catheter to puncture the mucosa of the gastrointestinal wall 506. A tunnel is then bored in the submucosa at the desired lead implantation site 508.

A first end of the lead remains within the tunnel created in the gastrointestinal wall. After boring the tunnel, the physician then directs the lead through the remainder of the gastrointestinal wall, exiting through the muscularis propria, adventitia, or serosal side 510. Once through the entire thickness of the gastrointestinal wall, the lead is navigated to a predetermined endpoint within the abdomen 512. When the lead has been placed in its operative position, the first end engages the gastrointestinal musculature while the second end rests at the predetermined endpoint within the abdomen. In one embodiment, the predetermined endpoint is within the peritoneal cavity of the patient. In another embodiment, the second end of the lead is navigated through the anterior abdominal wall of the patient and the predetermined endpoint is in the subcutaneous region of the abdomen.

In various embodiments, the physician's visualization of the catheter and lead during implantation is assisted by differing imaging techniques. In one embodiment, ultrasound imaging is used in conjunction with visual imaging to help guide placement. In another embodiment, radiologic imaging is used in conjunction with visual imaging to help guide placement. In another embodiment, fluoroscopy is used in conjunction with visual imaging to help guide placement.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of implanting electrically conductive leads in gastrointestinal musculature of a patient utilizing an endoscopic approach, comprising the steps of:
    inserting an endoscope into an esophagus of a patient;
    identifying a lower esophageal sphincter (LES);
    entering a gastrointestinal (GI) wall with an electrically conductive lead from a mucosal side by puncturing a mucosa of an anterior segment of a region encompassing the LES;
    creating a tunnel in a submucosa of the anterior segment of the region encompassing the LES, the tunnel exiting the GI wall through a muscularis propria, adventitia, or serosal side of a stomach of the patient;
    navigating the lead through the tunnel to an anterior abdominal wall; and
    exiting a second end of the lead through the anterior abdominal wall while leaving a first end of the lead in the gastrointestinal musculature of the patient within the tunnel, wherein the region encompassing the LES comprises an area 3 cm above and 3 cm below the LES.

2. The method of implanting electrically conductive leads in the gastrointestinal musculature utilizing an endoscopic approach of claim 1, wherein said tunnel created in the submucosa of the anterior segment of the LES is less than 5 cm in length.

3. The method of implanting electrically conductive leads in the gastrointestinal musculature utilizing an endoscopic approach of claim 1, wherein said tunnel created in the submucosa of the anterior segment of the LES is within the range of 1 cm to 5 cm in length.

4. The method of implanting electrically conductive leads in the gastrointestinal musculature utilizing an endoscopic approach of claim 1, wherein said first end of said lead is not anchored to a gastrointestinal tissue.

5. The method of implanting electrically conductive leads in the gastrointestinal musculature utilizing an endoscopic approach of claim 1, wherein said first end of said lead is anchored to a gastrointestinal tissue.

6. The method of implanting electrically conductive leads in the gastrointestinal musculature utilizing an endoscopic approach of claim 1, wherein said leads are adapted to electrically stimulate the gastrointestinal musculature in an amount effective to treat any one or combination of obesity and gastroesophageal reflux disease (GERD).

7. The method of implanting electrically conductive leads in the gastrointestinal musculature utilizing an endoscopic approach of claim 1, further comprising using magnetic, ultrasound, radiologic, or fluoroscopic imaging, or physical indicators, mechanical indicators, or auditory indicators, in addition to visual imaging to assist in lead navigation.

8. The method of implanting electrically conductive leads in the gastrointestinal musculature utilizing an endoscopic approach of claim 1, further comprising subcutaneously implanting an implantable pulse generator (IPG) proximate the lead exit point in the anterior abdominal wall.

9. The method of implanting electrically conductive leads in the gastrointestinal musculature utilizing an endoscopic approach of claim 8, further comprising attaching said second end of said lead with said IPG so that said lead can receive pulse signals from said IPG.

10. The method of implanting electrically conductive leads in the gastrointestinal musculature utilizing an endoscopic approach of claim 8, further comprising using wireless communication to transmit pulse signals from said IPG to said lead.

11. A method of implanting electrically conductive leads in the gastrointestinal musculature of a patient utilizing an endoscopic approach, comprising the steps of:
- inserting an endoscope into an esophagus of a patient;
- identifying a lower esophageal sphincter (LES);
- entering a gastrointestinal (GI) wall with an electrically conductive lead from a mucosal side by puncturing a mucosa of an anterior segment of a region encompassing the LES;
- creating a tunnel in a submucosa of the anterior segment of the region encompassing the LES, the tunnel exiting the GI wall through a serosal side of a stomach of the patient;
- navigating the lead through the tunnel to an anterior abdominal wall; and
- exiting a second end of the lead through the anterior abdominal wall while leaving a first end of the lead in the gastrointestinal musculature within the tunnel, wherein the region encompassing the LES comprises an area 3 cm above and 3 cm below the LES.

12. The method of implanting electrically conductive leads in the gastrointestinal musculature utilizing an endoscopic approach of claim 11, wherein the tunnel created in the submucosa of the anterior segment of the LES is equal to or greater than 5 cm in length.

13. The method of implanting electrically conductive leads in the gastrointestinal musculature utilizing an endoscopic approach of claim 11, wherein said first end of said lead is not anchored to a gastrointestinal tissue.

14. The method of implanting electrically conductive leads in the gastrointestinal musculature utilizing an endoscopic approach of claim 11, wherein said first end of said lead is anchored to a gastrointestinal tissue.

15. The method of implanting electrically conductive leads in the gastrointestinal musculature utilizing an endoscopic approach of claim 11, further comprising a step of insufflating the stomach.

16. The method of implanting electrically conductive leads in the gastrointestinal musculature utilizing an endoscopic approach of claim 11, further comprising the steps of:
- finding a site where the stomach is in cross-approximation with the anterior abdominal wall;
- securing the stomach with one or more anchors;
- exiting the serosal surface of the stomach proximate said site; and
- entering an anterior abdominal wall proximate said site.

17. The method of implanting electrically conductive leads in the gastrointestinal musculature utilizing an endoscopic approach of claim 11, wherein said leads are adapted to electrically stimulate the gastrointestinal musculature in a therapeutically effective amount to treat any one or combination of obesity and gastroesophageal reflux disease (GERD).

18. The method of implanting electrically conductive leads in the gastrointestinal musculature utilizing an endoscopic approach of claim 11, further comprising using magnetic, ultrasound, radiologic, or fluoroscopic imaging, or physical indicators, mechanical indicators, or auditory indicators, in addition to visual imaging to assist in lead navigation.

19. The method of implanting electrically conductive leads in the gastrointestinal musculature utilizing an endoscopic approach of claim 11, further comprising subcutaneously implanting an implantable pulse generator (IPG) proximate the lead exit point in the anterior abdominal wall.

20. The method of implanting electrically conductive leads in the gastrointestinal musculature utilizing an endoscopic approach of claim 19, further comprising attaching said second end of said lead with said IPG so that said lead can receive pulse signals from said IPG.

21. The method of implanting electrically conductive leads in the gastrointestinal musculature utilizing an endoscopic approach of claim 19, further comprising using wireless communication to transmit pulse signals from said IPG to said lead.

22. A method of implanting electrically conductive leads in the gastrointestinal musculature of a patient utilizing an endoscopic approach, comprising:
- inserting an endoscope into an esophagus of a patient;
- advancing said endoscope to an implantation site along a gastrointestinal tract of said patient;
- entering a gastrointestinal (GI) wall with an electrically conductive lead from a mucosal side by puncturing a mucosa of an anterior segment of said implantation site;
- creating a tunnel in a submucosa of the anterior segment of said implantation site, the tunnel exiting the GI wall through a muscularis propria, adventitia, or serosal side of a stomach of the patient;
- navigating a second end of said lead, exiting the GI wall through the tunnel, to a predetermined endpoint within an abdomen of said patient; and leaving a first end of said lead in the gastrointestinal musculature at said implantation site within the tunnel.

23. The method of implanting electrically conductive leads in the gastrointestinal musculature utilizing an endoscopic approach of claim 22, wherein said first end of said lead is not anchored to a gastrointestinal tissue.

24. The method of implanting electrically conductive leads in the gastrointestinal musculature utilizing an endoscopic approach of claim 22, wherein said first end of said lead is anchored to a gastrointestinal tissue.

25. The method of implanting electrically conductive leads in the gastrointestinal musculature utilizing an endoscopic approach of claim 22, wherein said predetermined endpoint is within a peritoneal cavity of said patient.

26. The method of implanting electrically conductive leads in the gastrointestinal musculature utilizing an endoscopic approach of claim 22, further comprising the step of navigating said second end of said lead through an anterior abdominal wall of said patient and wherein said predetermined endpoint is within a subcutaneous region of the abdomen.

27. The method of implanting electrically conductive leads in the gastrointestinal musculature utilizing an endoscopic approach of claim 22, further comprising using magnetic, ultrasound, radiologic, or fluoroscopic imaging, or physical indicators, mechanical indicators, or auditory indicators, in addition to visual imaging to assist in lead navigation.

28. The method of implanting electrically conductive leads in the gastrointestinal musculature utilizing an endoscopic approach of claim 22, wherein the leads are adapted to electrically stimulate the gastrointestinal musculature in a therapeutically effective amount to treat a condition of a gastrointestinal system of said patient.

29. The method of implanting electrically conductive leads in the gastrointestinal musculature utilizing an endoscopic approach of claim 28, wherein said condition includes obesity and gastroesophageal reflux disease (GERD).

30. The method of implanting electrically conductive leads in the gastrointestinal musculature utilizing an endoscopic approach of claim 22, further comprising implanting an implantable pulse generator (IPG) proximate said predetermined endpoint.

31. The method of implanting electrically conductive leads in the gastrointestinal musculature utilizing an endoscopic approach of claim 30, further comprising attaching said second end of said lead with said IPG such that said lead can receive pulse signals from said IPG.

32. The method of implanting electrically conductive leads in the gastrointestinal musculature utilizing an endoscopic approach of claim 30, further comprising using wireless communication to transmit pulse signals from said IPG to said lead.

* * * * *